United States Patent
Wu et al.

(10) Patent No.: US 11,180,736 B2
(45) Date of Patent: *Nov. 23, 2021

(54) METHOD OF PREPARING RECOMBINANT ADENO-ASSOCIATED VIRUS AND RECOMBINANT BACULOVIRUS

(71) Applicant: WUHAN INSTITUTE OF PHYSICS AND MATHEMATICS, CHINESE ACADEMY OF SCIENCES, Wuhan (CN)

(72) Inventors: Yang Wu, Wuhan (CN); Fuqiang Xu, Wuhan (CN); Xiaobin He, Wuhan (CN)

(73) Assignee: WUHAN INSTITUTE OF PHYSICS AND MATHEMATICS, CHINESE ACADEMY OF SCIENCES, Wuhan (CN)

(*) Notice: Subject to any disclaimer, the term of this patent is extended or adjusted under 35 U.S.C. 154(b) by 345 days.

This patent is subject to a terminal disclaimer.

(21) Appl. No.: 15/883,068

(22) Filed: Jan. 29, 2018

(65) Prior Publication Data

US 2018/0155697 A1 Jun. 7, 2018

Related U.S. Application Data

(63) Continuation-in-part of application No. PCT/CN2016/073246, filed on Feb. 3, 2016.

(30) Foreign Application Priority Data

Dec. 24, 2015 (CN) .......................... 201510988801.8

(51) Int. Cl.
C12N 15/86 (2006.01)
C12N 7/00 (2006.01)
C07K 14/005 (2006.01)

(52) U.S. Cl.
CPC .............. *C12N 7/00* (2013.01); *C12N 15/86* (2013.01); *C07K 14/005* (2013.01); *C12N 2710/14022* (2013.01); *C12N 2710/14044* (2013.01); *C12N 2750/14122* (2013.01); *C12N 2750/14143* (2013.01); *C12N 2800/22* (2013.01)

(58) Field of Classification Search
None
See application file for complete search history.

(56) References Cited

U.S. PATENT DOCUMENTS 10,501,758 B2 * 12/2019 Wu .......................... C12N 7/00

FOREIGN PATENT DOCUMENTS

CN 1570121 A * 1/2005
CN 1570121 A 1/2005

OTHER PUBLICATIONS

WIPO machine translation for CN 1570121 (obtained from <https://patentscope.wipo.int/beta/en/search.jsf> on Jan. 6, 2020, 10 pages) (Year: 2020).*
Kwon et al. (2007) Designer Gene Delivery Vectors: Molecular Engineering and Evolution of Adeno-Associated Viral Vectors for Enhanced Gene Transfer. Pharmaceutical Research, 25(3):489-499 (Year: 2007).*
Lubelski et al. (2014) Insect Cell-Based Recombinant Adeno-Associated Virus Production: Molecular Process Optimization. BioProcessing Journal, 13(3):6-11 (Year: 2014).*
Aslanidi et al. (2009) An inducible system for highly efficient production of recombinant adeno-associated virus (rAAV) vectors in insect Sf9 cells. PNAS, 106(13):5059-5064 (Year: 2009).*
Q. Lei et al., Establishment of production system of recombinant adeno-associated viruses based on baculoviruses, Journal of Zhejiang Sci-Tech University, Sep. 2010, pp. 773-778, vol. 27, No. 5, Zhejiang Sci-Tech University, China.
G. Aslanidi et al., An inducible system for highly efficient production of recombinant adeno-associated virus (rAAV) vectors in insect Sf9 cells, Proceedings of the National Academy of Sciences of the United States of America, Mar. 31, 2009, pp. 5059-5064, vol. 106, No. 13, United States National Academy of Sciences, United States.

* cited by examiner

*Primary Examiner* — Michael D Burkhart
(74) *Attorney, Agent, or Firm* — JCIP Global Inc.

(57) ABSTRACT

A method for producing a recombinant adeno-associated virus (rAAV) and a recombinant baculovirus virus, the method including: (1) infecting an insect host packaging cell line with a corresponding recombinant baculovirus integrated with an rAAV genome ITR-GOI (gene of interest flanked by AAV inverted terminal repeats) and an AAV Cap gene or AAV Rep gene; (2) culturing the host packaging cell line infected with the recombinant baculovirus, so as to produce the recombinant adeno-associated virus; and (3) separating and purifying the recombinant adeno-associated virus obtained in (2).

12 Claims, 14 Drawing Sheets

Specification includes a Sequence Listing.

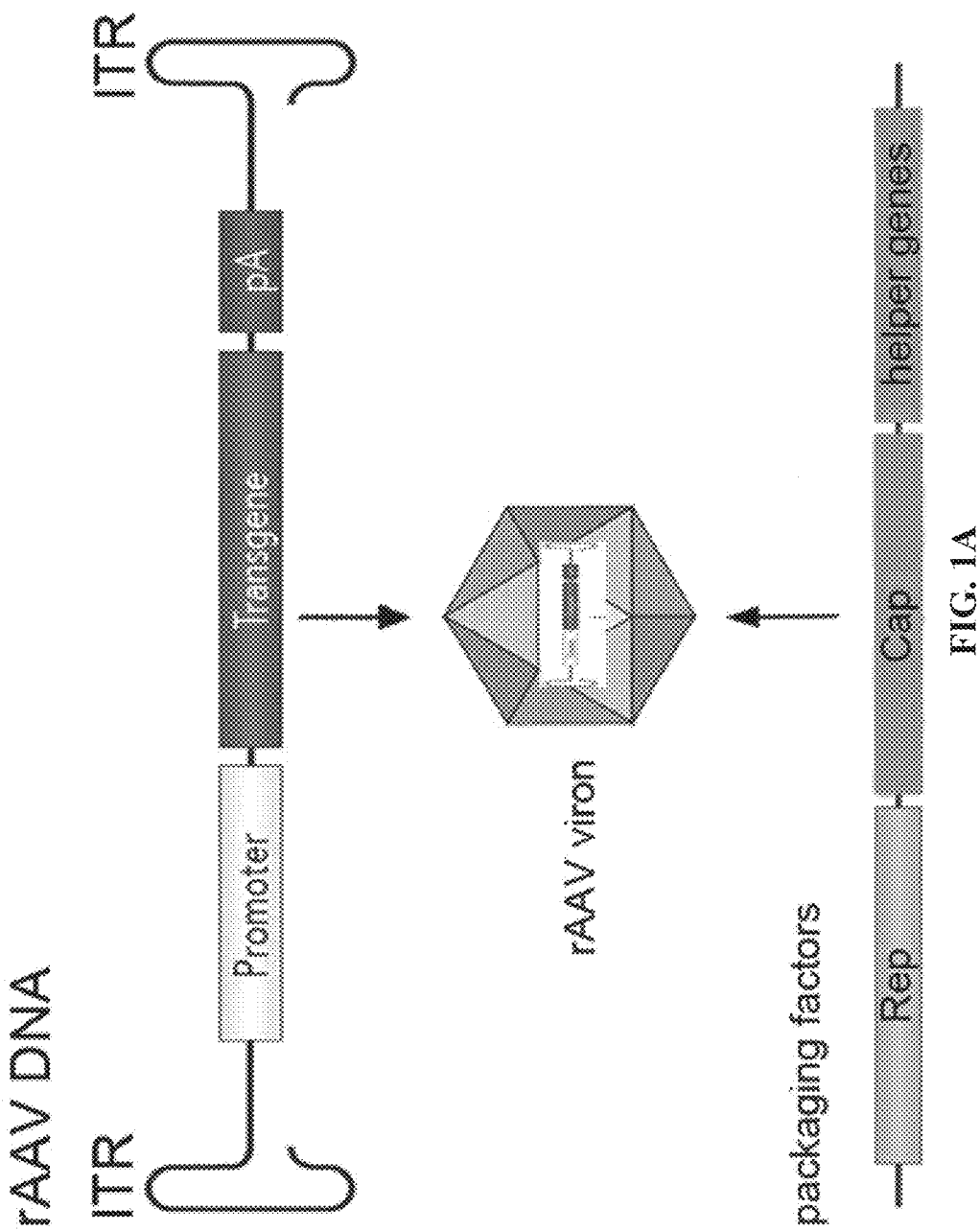

FIG. 6B

METHOD OF PREPARING RECOMBINANT ADENO-ASSOCIATED VIRUS AND RECOMBINANT BACULOVIRUS

CROSS-REFERENCE TO RELATED APPLICATIONS

This application is a continuation-in-part of International Patent Application No. PCT/CN2016/073246 with an international filing date of Feb. 3, 2016, designating the United States, now pending, and further claims foreign priority benefits to Chinese Patent Application No. 201510988801.8 filed Dec. 24, 2015. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND OF THE INVENTION

Field of the Invention

The disclosure relates to bioengineering, and more particularly relates to a method for preparing a recombinant adeno-associated virus and a recombinant baculovirus.

Description of the Related Art

Recombinant adeno-associated virus (rAAV) is one of the most promising vectors in the field of gene therapy due to its high safety, low immunogenicity, wide host range, and ability to mediate long-term expression of foreign genes in animals.

At present, there are two main methods for preparing rAAV on a large scale by the baculovirus expression system: Two-Bac system and One-Bac system based on Sf9/Rep-Cap packaging cell line. In Two-Bac system, one baculovirus genome integrates the AAV Rep and Cap genes and another baculovirus genome integrates the rAAVgenome ITR-GOI (gene of interest flanked by AAV inverted terminal repeats). The two recombinant baculoviruses co-infect host Sf9 cells and produce rAAV. In One-Bac system based on Sf9/Rep-Cap packaging cell line, the packaging cell line Sf9/Rep-Cap integrated both the Rep and Cap gene inducible expression cassettes. The Rep gene or Cap gene is under the control of the baculovirus late polyhedron (PH) promoter, and hr2 enhancer sequence and the AAV Rep protein binding sequence (RBE) are added upstream of the PH promoter. The Rep and Cap genes in packaging cell lines are expressed to produce rAAV after infection of the cell lines with a recombinant baculovirus that contains the rAAV genome ITR-GOI.

However, for the Two-Bac system, the yield of rAAV is not high because the two baculoviruses co-infect the cells at a low efficiency and cannot fully utilize the capacity of each cell. The two baculoviruses infection is a randomized process which is difficult to be optimized and lead to unstable rAAV quality in different production batches. For the One-Bac system based on Sf9/Rep-Cap packaging cell line, it is difficult to obtain high efficiency packaging cell line integrated both Rep gene and Cap genes, and it is not versatile to establish different kinds of cell lines carrying different Cap genes for the production of different serotypes of rAAV. This One-Bac system is not widely used because lack of flexibility and versatility.

THE DESCRIPTION OF THE INVENTION

In view of the above-described problems, it is an objective of the invention to provide a method for producing a recombinant adeno-associated virus for gene therapy and a recombinant baculovirus. One objective of the invention is to provide a recombinant adeno-associated virus for gene therapy by transforming the AAV Rep gene, Cap gene, and rAAV genome ITR-GOI into the baculovirus genome or into the genome of the host packaging cell for production of rAAV through a recombinant baculovirus-infected host packaging cell line, thereby resolving the problems of high complexity, low flexibility, and low versatility in existing method for large-scale production of rAAV.

To achieve the above objective, according to one aspect of the invention, there is provided a method for producing a recombinant adeno-associated virus, the method comprising:

1) infecting a host packaging cell line with a recombinant baculovirus in which a rAAV genome ITR-GOI and a Cap gene or a Rep gene are integrated;
2) culturing the host packaging cell line infected with the recombinant baculovirus in (1) to produce recombinant adeno-associated virus; and
3) isolating and purifying the recombinant adeno-associated virus obtained in (2).

In a class of this embodiment, step (1) comprises utilizing pFast. Bac. Dual shuttle vector to construct the recombinant baculovirus.

In a class of this embodiment, step (1) is operated as follows:

a. ITR-GOI is cloned into an intermediate sequence between P10 promoter and PH promoter of the pFast. Bac. Dual shuttle vector; the P10 has a sequence as follows (SEQ ID No. 8):

ATACGGACCTTTAATTCAACCCAACACAATATATTATAGTTAAATAAGAA

TTATTATCAAATCATTTGTATATTAATTAAAATACTATACTGTAAATTAC

ATTTTATTTACAATCACTCGAC;

PH promoter has a sequence as follows (SEQ ID No. 9):

ATCATGGAGATAATTAAAATGATAACCATCTCGCAAATAAATAAGTATTT

TACTGTTTTCGTAACAGTTTTGTAATAAAAAAACCTATAAATATTCCGGA

TTATTCATACCGTCCCACCATCGGGCGC;

The intermediate sequence has a sequence as follows (SEQ ID No. 10):

ACTCCGGAATATTAATAG;

b. The Cap gene or Rep gene is cloned into a multiple cloning site downstream of the P10 promoter or the PH promoter of the pFast. Bac. Dual shuttle vector to obtain a corresponding shuttle plasmid.

In a class of this embodiment, the recombinant adeno-associated virus ITR core expression cassette carries a gene of interest.

In a class of this embodiment, the host packaging cell line is used for facilitating the replication and assembly of the recombinant adeno-associated virus.

In a class of this embodiment, the host packaging cell line comprises expression cassette inducing expression of the Rep gene or the Cap gene.

According to another aspect of the invention, there is provided a recombinant baculovirus that comprises the rAAV genome ITR-GOI and the Cap gene of the corresponding serotype.

In a class of this embodiment, the Cap gene has a sequence which is a codon-optimized sequence based on the ribosomal leaky scanning principle.

According to another aspect of the invention, there is provided a recombinant baculovirus that comprises the rAAV genome ITR-GOI and the Rep gene of the corresponding serotype.

In a class of this embodiment, the Rep gene has a sequence which is a codon-optimized sequence based on the ribosome leaky scanning principle.

In general, compared with the prior art, the recombinant baculovirus and preparation method thereof of the disclosure has advantages summarized as follows:

By placing the AAV Cap gene (or Rep gene) and the ITR core expression cassette in a recombinant baculovirus, the Rep gene (or Cap gene) is integrated into the host cell genome, and the host packaging cell line supports packaging rAAV. Compared with current One-Bac system methods in which both the Rep and Cap genes are integrated into host packaging cell lines by, the method of the invention is much less difficult in constructing the packaging cell lines. In particular, in the invention's method, the Cap gene and ITR-GOI are placed in a baculovirus genome. Because the Rep gene of type 2 AAV is able to assist packaging of various serotypes of rAAV, a Sf9/Rep2 packaging is sufficient for producing various serotypes of rAAV, which leads to high flexibility and versatility of the method.

BRIEF DESCRIPTION OF DRAWINGS

FIG. 1A is a schematic diagram of the packaging of rAAV;

FIG. 6B is fluorescence microscopy images of rAAV-infected HEK293 and Sf9 cells prepared in Example 3;

DETAILED DESCRIPTION OF THE EMBODIMENTS

Figure 1B:
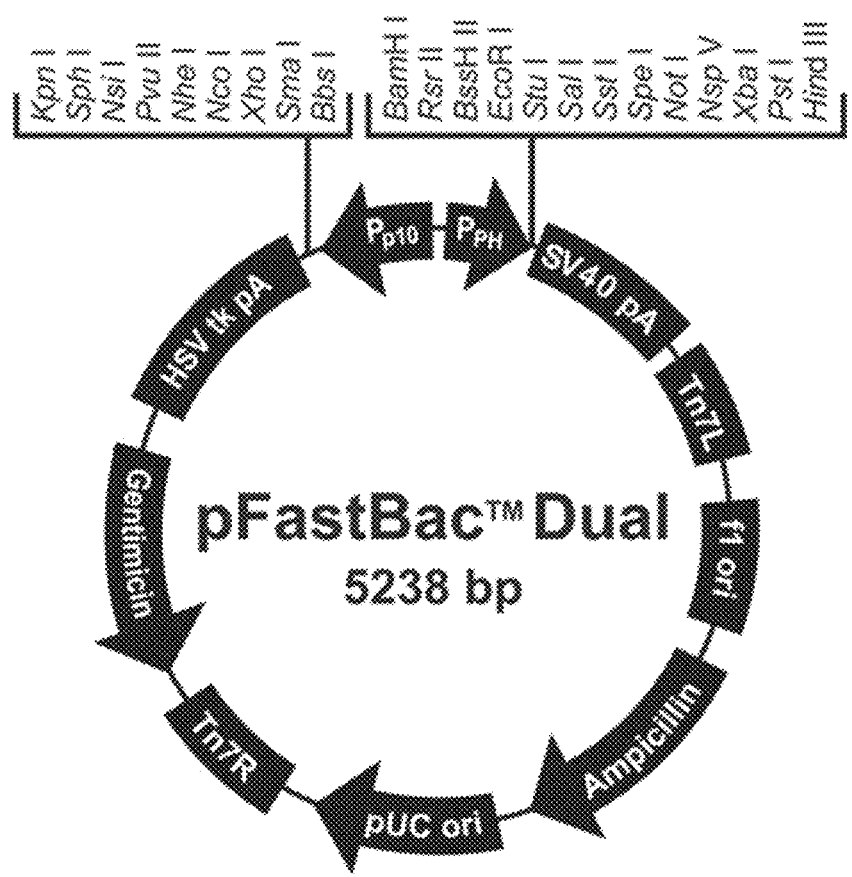
FIG. 1B is a schematic diagram of the structure of the pFast. Bac. Dual (pFBD) shuttle plasmid in Bac-to-Bac system.

To make the objectives, technical solutions, and advantages of the invention more comprehensible, the invention is further described in detail below with reference to the accompanying drawings and embodiments. It should be understood that the specific embodiments described herein are merely used to explain the invention, and are not intended to limit the invention. In addition, the technical features involved in the various embodiments of invention described below can be combined with each other as long as the two do not conflict with each other.

The method of the invention for preparing a recombinant adeno-associated virus comprises the following steps:

(1) a host packaging cell line is infected with a recombinant baculovirus in which a rAAV genome ITR-GOI and a Cap gene or a Rep gene are integrated;

The recombinant baculovirus is used to provide ITR-GOI and Cap or Rep genes required for rAAV production. By activing the baculovirus specific promoters PH or P10 after infected with the baculovirus, the host packing cell is induced to express the Rep gene or Cap gene so as to facilitate the replication and assembly of rAAV.

The recombinant baculovirus is preferably a pFast. Bac. Dual (pFBD) shuttle vector of the Bac-to-Bac system (see, FIG. 1B) built as follows:

i. The ITR-GOI is cloned into an intermediate sequence between the P10 promoter and the PH promoter of the pFBD vector.

ii. The Cap gene or Rep gene is cloned into a multiple cloning site downstream of the P10 promoter or the PH promoter to obtain a corresponding shuttle plasmid.

iii. The corresponding recombinant baculovirus is prepared according to Bac-to-Bac system method.

The ITR-GOI is linked to the expression cassette of the Cap gene or Rep gene by a 5' terminal ligation nucleic acid segment or a 3' terminal ligation nucleic acid segment. The gene of interest (GOI) is flanked by a pair of AAV inverted terminal repeats (ITR). The ITR-GOI expression cassette used with a GFP gene expression cassette containing CMV promoter, GFP gene, and ploy (PA) in the examples.

The Cap gene encodes the three structural proteins VP1, VP2, VP3 of AAV which constitute the virus capsid. AAV binds to the surface of host cells through the binding of the capsid protein to the receptors on the cell surface. The tissues and cells tropisms among AAVs of different serotypes mainly due to the difference in the Cap genes among different serotypes. Therefore, for the production of different serotypes of rAAV, it is necessary to use the corresponding serotype of the Cap gene. The Cap gene was codon-optimized based on the principle of ribosomal leaky scanning One mRNA is obtained by the transcription through P10 promoter or PH promoter to achieve expression of the capsid proteins of VP1, VP2, and VP3 near natural ratio (1:1:10).

The Rep gene encodes the four nonstructural proteins Rep78, Rep68, Rep52, and Rep40 of AAV, which are mainly responsible for the replication of the viral genome, transcriptional regulation, site-specific integration, and the like. Presently, rAAVs of different serotypes are usually produced using the Rep gene of serotype 2 AAV. The Rep gene was codon-optimized based on the principle of ribosomal leaky scanning, and anmRNA was transcribed through the P10 promoter or the PH promoter to achieve the functional expression of the Rep gene.

The recombinant baculovirus of the invention can be prepared according to the following process:

A. The codon-optimized Cap and Rep genes are obtained by gene synthetic methods;

ITR-GOI is obtained by conventional molecular biology techniques.

B. The ITR-GOI and the Cap gene or Rep gene obtained in step A are integrated into pFast. Bac. Dual (pFBD) shuttle vector by molecular cloning to obtain a recombinant baculovirus according to the Bac-to-Bac system protocol.

The host packaging cells, preferably Sf9 cells, are used in the replication and assembly of rAAV. Preferably, when the recombinant baculovirus does not contain the Rep gene, the host cell's genome needs to contain the Rep gene expression cassette; when the recombinant baculovirus does not contain the Cap gene, the host cell's genome needs to contain the Cap gene expression cassette. The gene expression cassettes random integrated in the host cell genome were transfected by plasmids contain the corresponding gene expression cassettes.

Figure 2A:
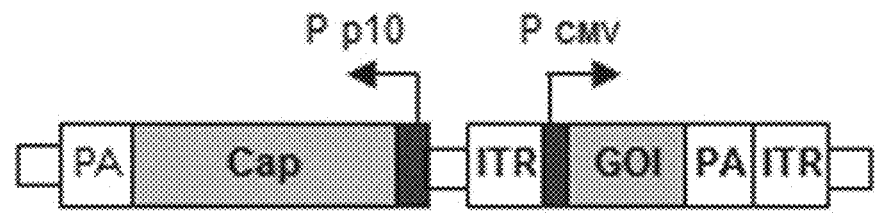
FIG. 2A is a schematic diagram of the structure of the recombinant shuttle plasmid pFD/Cap-(ITR-GFP) in Example 1.
Figure 2B:
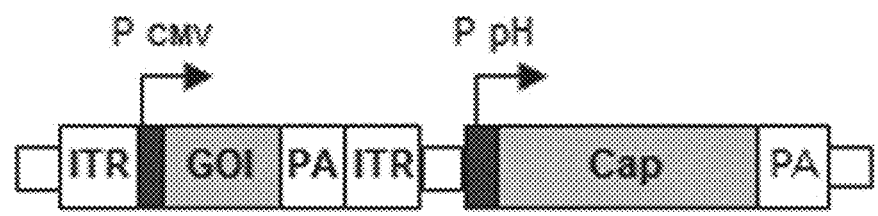
FIG. 2B is a schematic diagram of the structure of the recombinant shuttle plasmid pFD/Cap-(ITR-GFP) in Example 2.
Figure 2C:
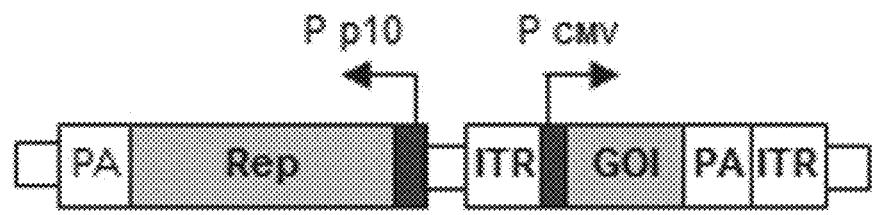
FIG. 2C is a schematic diagram of the structure of the recombinant shuttle plasmid pFD/Rep-(ITR-GFP) in Example 3.
Figure 2D:
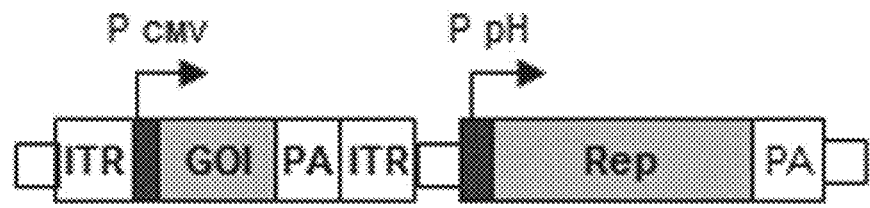
FIG. 2D is a schematic diagram of the structure of the recombinant shuttle plasmid pFD/Rep-(ITR-GFP) in Example 4.
Figure 2E:
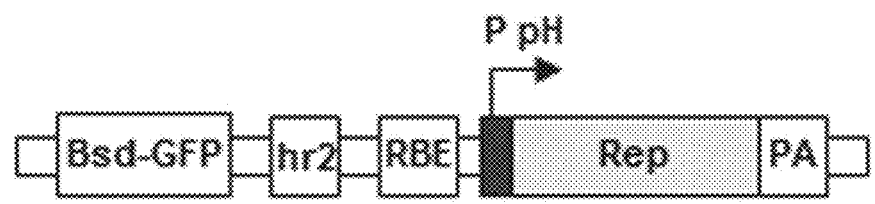
FIG. 2E is a schematic diagram of the structure of the pIR-rep78-hr2-RBE-bsd-GFP plasmid used to create the Sf9/Rep packaging cell line in Examples 1 and 2.

The host cells, preferably Sf9 cells, that is integrated with the Rep gene inducible expression cassette, are prepared as follows: First, in the pIR-rep78-hr2-RBE plasmids (see, Proc Natl Acad Sci USA. 2009 Mar. 31; 106 (13): 5059-64), the green fluorescent protein (GFP) gene is fused with FMDV self-cleaving peptide 2A to the C-terminus of blasticidin (Bsd), as shown in FIG. 2E. Then, the reconstructive plasmid is transfected into Sf9 cells and screened by Bsd antibiotics to obtain an Sf9/Rep packaging cell line. The cell line constitutively expresses GFP and can be further isolated by monoclonal isolation or flow cytometry to obtain an Sf9/Rep packaging cell line with high yield of rAAV.

Figure 2F:
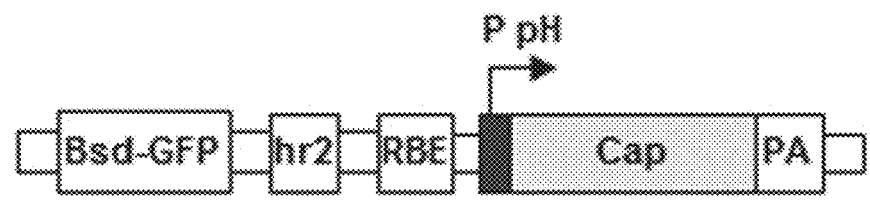
FIG. 2F is a schematic diagram of the structure of the pIR-VP-hr2-RBE-bsd-GFP plasmid used to create the Sf9/Cap packaging cell line in Examples 3 and 4.

The host cells, preferably Sf9 cells, which is integrated with the Cap gene inducible expression cassette, are prepared as follows: First, in the recombinant plasmid pIR-VP-hr2-RBE (see, Proc Natl Acad Sci USA. 2009 Mar. 31; 106 (13): 5059-64), the GFP gene is fused with FMDV self-cleaving peptide 2A to the C-terminus of the blasticidin (Bsd) gene, as shown in FIG. 2F. Then, the reconstructive plasmid is transfected into Sf9 cells and screened by Bsd antibiotics to obtain the Sf9/Cap packaging cell line. This cell line constitutively expresses GFP and can be further isolated by monoclonal isolation or flow cytometry to obtain a Sf9/Cap packaging cell line with a high yield of rAAV.

Because the gene integration is random, the host cell is transfected with plasmids and then screened with antibiotics. Only the high copy number of gene integrated cell allows for high level expression of integrated helper genes including the reporter gene GFP after being infected by the baculovirus. There may be at least one copy of the expression cassette for the Rep gene or Cap gene, or may be multiple copies thereof in the cell genome after random integration and screening of antibiotics. However, the advantages or disadvantages of the packaging cell line (the level of rAAV production) are not absolutely related to the integrated gene copy number. Therefore, the performance of the packaging cell line can be evaluated by the yield of the rAAV after infected by the recombinant baculovirus.

Figure 3A:
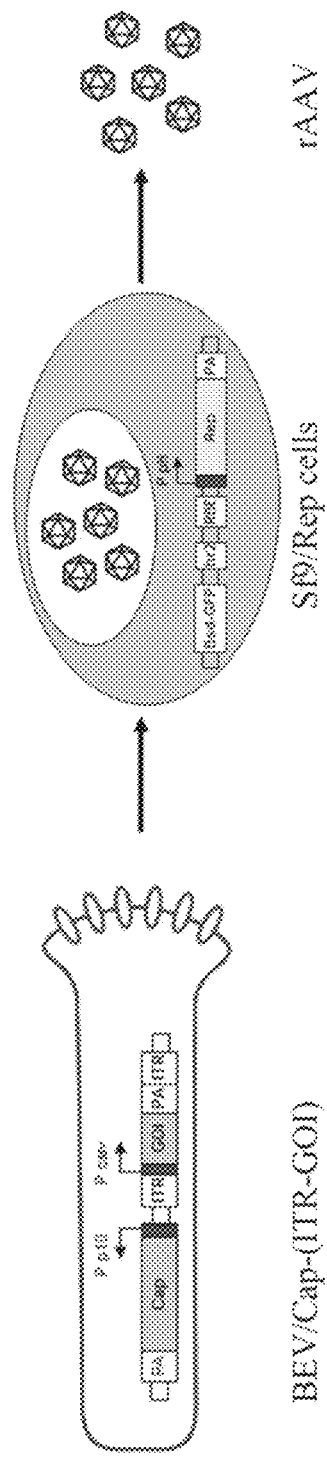
FIG. 3A is a schematic diagram of a process of producing rAAV by using a recombinant baculovirus to infect a host packaging cell line in Example 1 and Example 2.
Figure 3B:
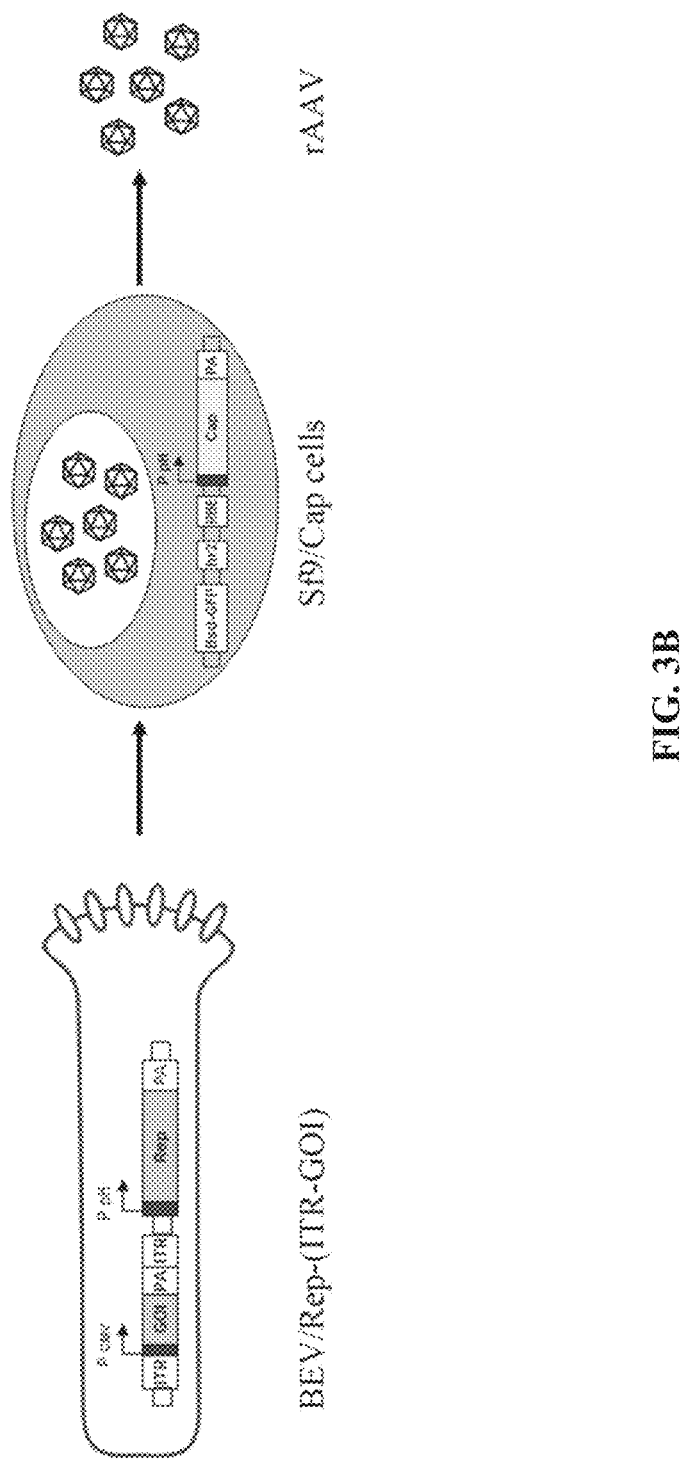
FIG. 3B is a schematic diagram of a process of producing rAAV by using a recombinant baculovirus to infect a host packaging cell line in Example 3 and Example 4.

The corresponding host packaging cell line is infected with the recombinant baculovirus (BEV) as described above (FIG. 3).

(2) The host packaging cell line infected with the recombinant baculovirus in (1) is cultured to produce a large amount of rAAV.

Specifically, the following steps are performed: The host packaging cells are suspension cultured in shake flasks until the cell density reached $3 \times 10^6$ cells/ml and are infected by the recombinant baculovirus (BEV) at a multiplicity of infection (MOI) of 5, and are then cultured at 27° C. and 120 rpm for 3 days after infection. The cell suspension is centrifuged at 3000 rpm for 5 minutes, and the culture supernatant and cell pellet are collected.

(3) The recombinant adeno-associated virus obtained in (2) is separated and purified.

rAAV is mainly found in the cell pellets. The rAAV is purified for further use. The detailed method steps can be found in (J Virol Methods, 2007. 139 (1): 61-70, J Virol Methods, 2012. 179 (1): 276-80).

The recombinant baculovirus provided by the invention is characterized in that its genome contains a rAAV genome ITR-GOI and a Cap gene or a Rep gene of a corresponding serotype. The sequence of the Cap gene or Rep gene is a codon-optimized sequence based on the ribosomal leaky scanning principle.

The examples based on type A adeno-associated virus (AAV2) are as follows:

Example 1

Preparation of rAAV by Infecting Sf9/Rep Packaging Cell Line With BEV/Cap-(ITR-GFP)

(1) The corresponding host packaging cell line was infected with the recombinant baculovirus contained rAAV genome ITR-GFP and the Cap gene of the corresponding serotype.

The recombinant baculovirus, i.e., recombinant BEV/Cap-(ITR-GFP), integrated with the rAAV genome ITR-GFP and the Cap gene of the corresponding serotype, was prepared and amplified as follows:

To place the ITR-GFP and the Cap gene in a recombinant baculovirus, pFast. Bac. Dual (pFBD) shuttle vector was used (FIG. 1B). In the example, the Cap gene of the serotype 2 AAV was codon optimized based on the ribosomal leaky scanning principle and the Cap gene was placed under the control of the P10 promoter (as in Scheme 1, FIG. 2A) or the PH promoter (Scheme 2, as shown in FIG. 2B) so that the three capsid proteins of VP1, VP2, and VP3 are expressed near the natural ratio (1:1:10). The Cap gene sequence is SEQ ID No. 1 or SEQ ID No. 2 (CapA or CapB). The ITR-GFP is the nucleic acid sequence of serotype 2 AAV, i.e., the sequence of SEQ ID No. 3, and contains an expression cassette of GFP. CMV promoter controls the expression of GFP so as to allow for easy detection of the recombinant virus activity. The ITR-GFP is linked to the Cap gene expression cassette or the vector via a 5' terminal ligation nucleic acid fragment or a 3' terminal ligation nucleic acid fragment. The 5' terminal ligation nucleic acid fragment or the 3' terminal ligation nucleic acid fragment is a sequence of SEQ ID No. 4 (link A) or SEQ ID No. 5 (link B).

In this example, the recombinant baculovirus may have one of the structures as follows:

CapA-LinkA-(ITR-GFP)-linkB

A recombinant shuttle plasmid pFBD/Cap-(ITR-GFP) was constructed by placing the ITR-GFP on one side of the pFBD/Cap vector via a ligation nucleic acid fragment using conventional molecular cloning techniques.

The recombinant shuttle plasmid was transformed into DH10Bac containing the AcMNPV baculovirus genome according to the Bac-to-Bac system protocol. Recombinant baculovirus genome (Bacmid) was obtained by Tn7 transposon element-mediated recombination. Positive bacteria containing recombinant Bacmid were obtained by blue-white screening and PCR identification. Recombinant Bacmid was extracted and purified and transfected into adherently cultured Sf9 cells. Sf9 cells were completely infected with recombinant baculovirus and showed obvious cytopathic effect (CPE). The cell culture was centrifuged at 3000 rpm for 5 min, and the resulting recombinant baculovirus was contained in the supernatant.

The supernatant was used to infect adherently cultured Sf9 cells and cultured for 3 days. The control group of uninfected Sf9 cells were in the normal state without GFP expression, while the Sf9 cells infected with the recombinant BEV/Cap-(ITR-GFP) had a significant CPE phenomenon and obvious GFP expression, as the results shown in FIG. 4A. Three days after infection, the cell culture supernatant was centrifuged at 3000 rpm for 5 min, and the BEV supernatant was obtained. The titer of the BEV was determined by the method of Fluorescent Quantitative-PCR. See, Proc Natl Acad Sci USA, 2009. 106 (13): 5059-64.

Figure 4A:
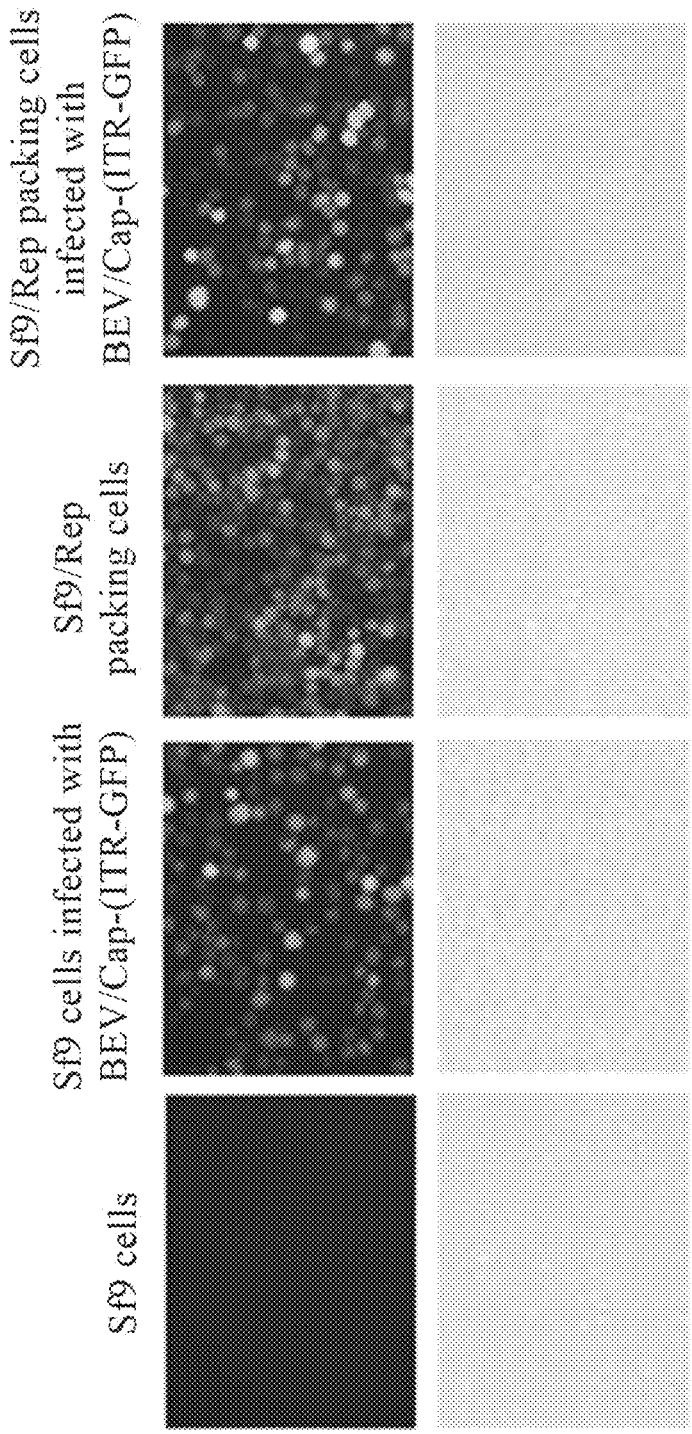
FIG. 4A is fluorescence microscopy images of Sf9 cells and Sf9/Rep packing cells uninfected or infected with recombinant baculovirus BEV/Cap-(ITR-GFP) in Example 1.

The corresponding host packaging cell line, i.e., the Sf9/Rep packaging cell line inducible expression of the Rep gene, was established as follows:

To facilitate the screening of packaging cell lines, the existing pIR-rep78-hr2-RBE plasmid (see, Proc Natl Acad Sci USA, 2009. Mar. 31; 106 (13): 5059-64) was modified: the C-terminus of the blasticidin (Bsd) gene was fused to the GFP gene by FMDV self-cleaving peptide 2A to obtain the pIR-rep78-hr2-RBE-bsd-GFP plasmid (FIG. 2E). Then, the modified plasmid was transfected into Sf9 cells, and the Sf9/Rep packaging cell line integrated with the Rep gene expression cassette was obtained by Bsd antibiotic screening. This cell line constitutively expresses GFP and can be further isolated by monoclonal isolation or by flow cytometry to obtain an Sf9/Rep packaging cell line with a higher yield of rAAV, as shown in FIG. 4A.

(2) rAAV was produced via infecting the Sf9/Rep cell line with BEV/Cap-(ITR-GFP) and its activity was verified.

The cultured Sf9/Rep cell lines were infected with BEV/Cap-(ITR-GFP) at MOI=5. Three days after infection, the cell culture was centrifuged at 3000 rpm for 5 minutes to collect the culture supernatant and the cell pellet. The BEV was released mainly in the supernatant of the culture medium, and some of the un-released BEV was also present in Sf9/Rep cells. The rAAV was mainly existed in the nuclei of Sf9/Rep cells and some rAAV was released into the supernatant because of CPE, as shown in FIG. 4A. As a result, BEV and rAAV were existed in both supernatants and cell pellets.

Figure 4B:
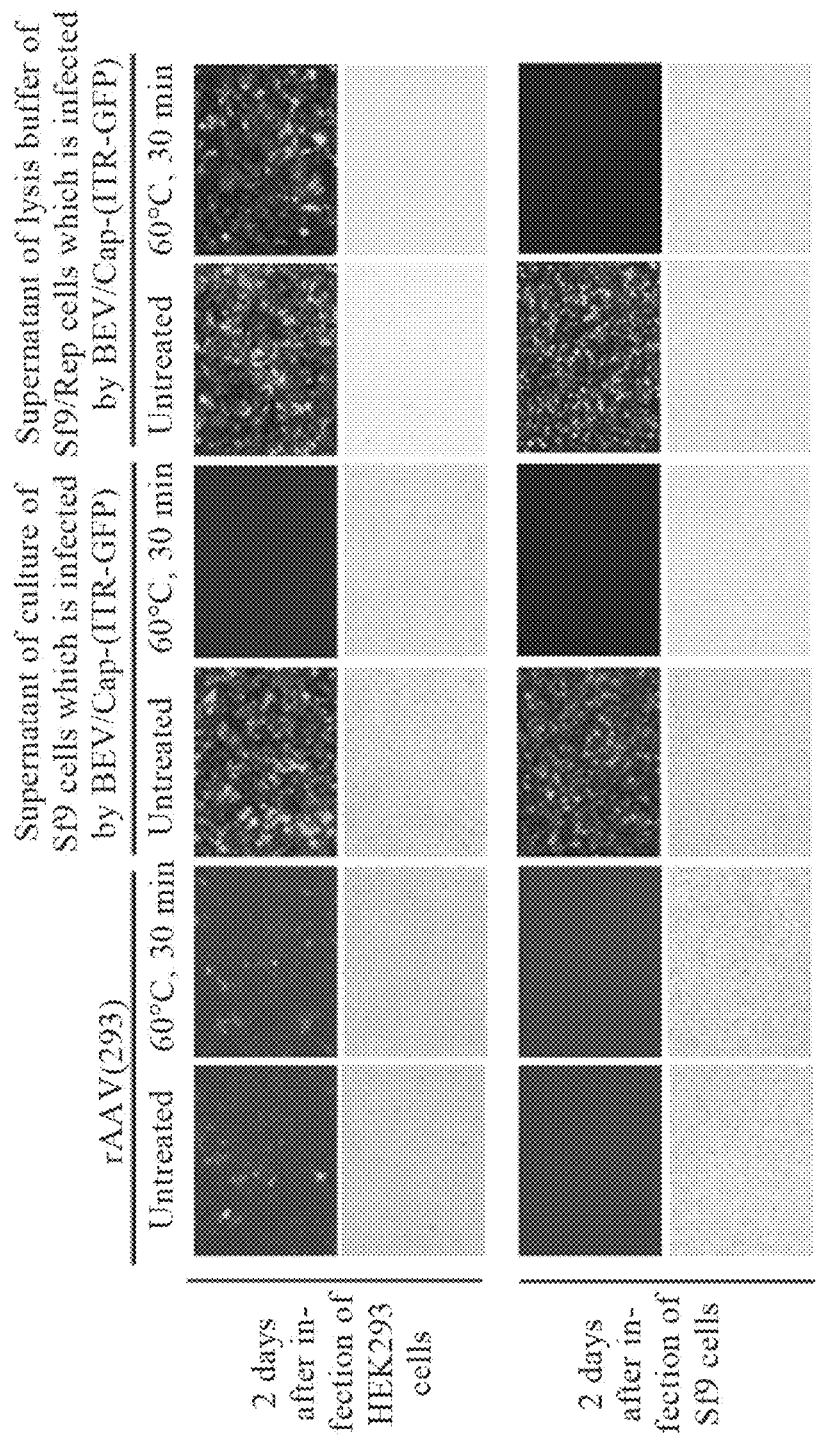
FIG. 4B is fluorescence microscopy images of rAAV-infected HEK293 and Sf9 cells prepared in Example 1.

In order to verify the production of rAAV by infecting Sf9/Rep cells with the BEV/Cap-(ITR-GFP), we use a simple HEK293 cells and Sf9 cells-based infection assay to test the AAV activity. The experimental results are shown in FIG. 4B. The detailed process and the results are as follows: The cell pellet were lysed by freeze-thaw using liquid nitrogen and a 37° C. water bath for three times, then centrifuged at 5000 rpm for 5 min and supernatant of cell lysis was collected. Because rAAV was enveloped, its activity was not affected by heating at 60° C. for 30 minutes, whereas recombinant baculovirus (BEV) was enveloped and lost its activity after treatment at 60° C. for 30 minutes. For rAAV2 (293 cells derived) samples, in 293 cells-based infection assays, both the treated and untreated can express GFP. In Sf9 cells-based infection assays, both the treated and untreated cannot express GFP. It indicates that rAAV2 do not infect Sf9 cells. For BEV/Cap2-(ITR-GFP) samples, both in 293 cells and Sf9 cells-based infection assays, only the untreated can express GFP, while the treated cannot express GFP. For the BEV/Cap2-(ITR-GFP) infected Sf9/Rep cell lysate supernatant samples, which contain some non-secrete BEVs and the major rAAV. In 293 cells-based infection assays, both the treated and untreated can express GFP, but the treated expressing GFP decrease slightly. It indicates that there are a lot of rAAV2 expressing GFP. In Sf9 cells-based infection assays, the untreated can express GFP, while the treated cannot express GFP.

(3) The recombinant adeno-associated virus obtained in (2) was isolated and purified.

Purification, titer determination and cell-level transduction activity validation of rAAV:

About $1\times10^8$ Sf9/Rep cells was collected after recombinant BEV infection. After adding 10 ml of lysis buffer (50 mM Tris-Cl, 150 mM NaCl, 2 mM $MgCl_2$, pH 8.0), the cell pellets were lysed by freeze-thaw using liquid nitrogen and a 37° C. water bath for three times, and then centrifuged at 5000 rpm for 5 min. The supernatant was collected, and nuclease Benzonase was added to the supernatant to a final concentration of 50 U/ml. The mixture was incubated in water bath at 37° C. for 60 min. After centrifugation at 5000 rpm for 10 min, the supernatant was collected. The supernatant was extracted with chloroform and the extracted supernatant was further purified by two-phase precipitation with a solution containing 13.2% $(NH_4)_2SO_4$ and 10% PEG8000 (J Virol Methods, 2007. 139 (1): 61-70, J Virol Methods, 2012. 179 (1): 276-80). The two-phase precipitated supernatant was dialyzed and desalted with a PBS solution and concentrated to a final volume of 1 ml by an Amicon ultra-4 (100 kD cutoff) dialysis column and stored at −80° C. after aseptic aliquots. The titer of rAAV was determined by fluorescence quantitative PCR, and the titer unit was expressed as virus genome (VG)/ml.

The rAAV yield of the purification process is shown in Table 1. The experimental results showed that the yield of rAAV in a single Sf9/Rep packaging cell was up to $8.62\times10^4$ VG. After the purification, the recovery rate reached 36.9%.

TABLE 1 rAAV purification process yield analysis

| Purification step | Volume (mL) | rAAV concentration (VG/mL) | rAAV amount (VG) | rAAV yield (%) |
| --- | --- | --- | --- | --- |
| Lysate treated supernatant | 20 | $4.31 \times 10^{11}$ | $8.62 \times 10^{12}$ | 100 |
| Chloroform treated supernatant | 20 | $3.42 \times 10^{11}$ | $6.84 \times 10^{12}$ | 79.4 |
| two-phase precipitated supernatant | 27 | $2.15 \times 10^{11}$ | $5.81 \times 10^{12}$ | 67.4 |
| Dialysis treated supernatant | 1 | $3.18 \times 10^{12}$ | $3.18 \times 10^{12}$ | 36.9 |

Figure 4C:
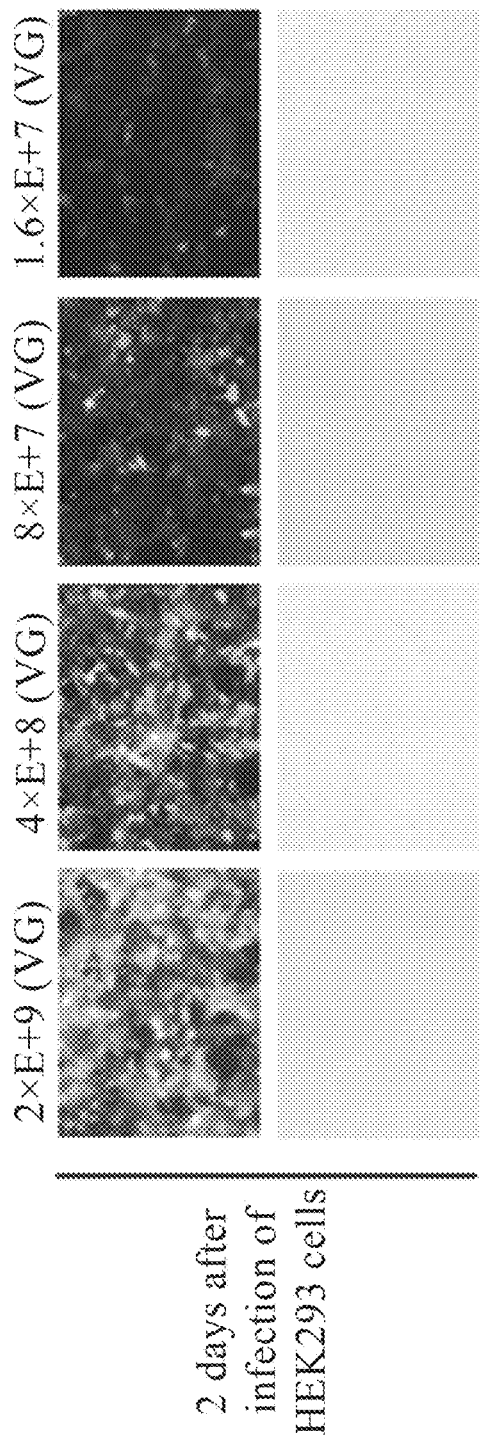
FIG. 4C is fluorescence microscopy images of a purified rAAV-infected HEK293 cell in Example 1.

HEK293 cells were seeded into 96-well plates at $1\times10^4$ cells/well and were infected with the purified rAAV of corresponding concentration gradient. 48 h after infection, GFP expression was observed by fluorescence microscopy, as shown in FIG. 4C. The results show that rAAV prepared by the method of the invention has good cell-level transduction activity.

Example 2

Preparation of rAAV by Infection of Sf9/Rep Packaging Cell Line With Recombinant BEV/Cap-(ITR-GFP)

This example is similar to Example 1 except that the recombinant baculovirus has the following main components:

LinkA-(ITR-GFP)-linkB-CapB

After infecting the Sf9/Rep packaging cell line with the recombinant BEV/Cap-(ITR-GFP) in this example, the produced rAAV was purified. The rAAV yield of the purification process is shown in Table 2. The experimental results showed that the yield of rAAV in a single Sf9/Rep packaging cell was up to $7.20 \times 10^4$ VG. After purification by this method, the yield of rAAV reached 31.3%.

TABLE 2 rAAV purification process yield analysis

| Purification step | Volume (mL) | rAAV concentration (VG/mL) | rAAV amount (VG) | rAAV yield (%) |
|---|---|---|---|---|
| Lysate treated supernatant | 20 | $3.60 \times 10^{11}$ | $7.20 \times 10^{12}$ | 100 |
| Chloroform treated supernatant | 20 | $2.79 \times 10^{11}$ | $5.58 \times 10^{12}$ | 77.5 |
| two-phase precipitated supernatant | 28 | $1.75 \times 10^{11}$ | $4.90 \times 10^{12}$ | 68.1 |
| Dialysis treated supernatant | 1 | $2.25 \times 10^{12}$ | $2.25 \times 10^{12}$ | 31.3 |

Figure 5:
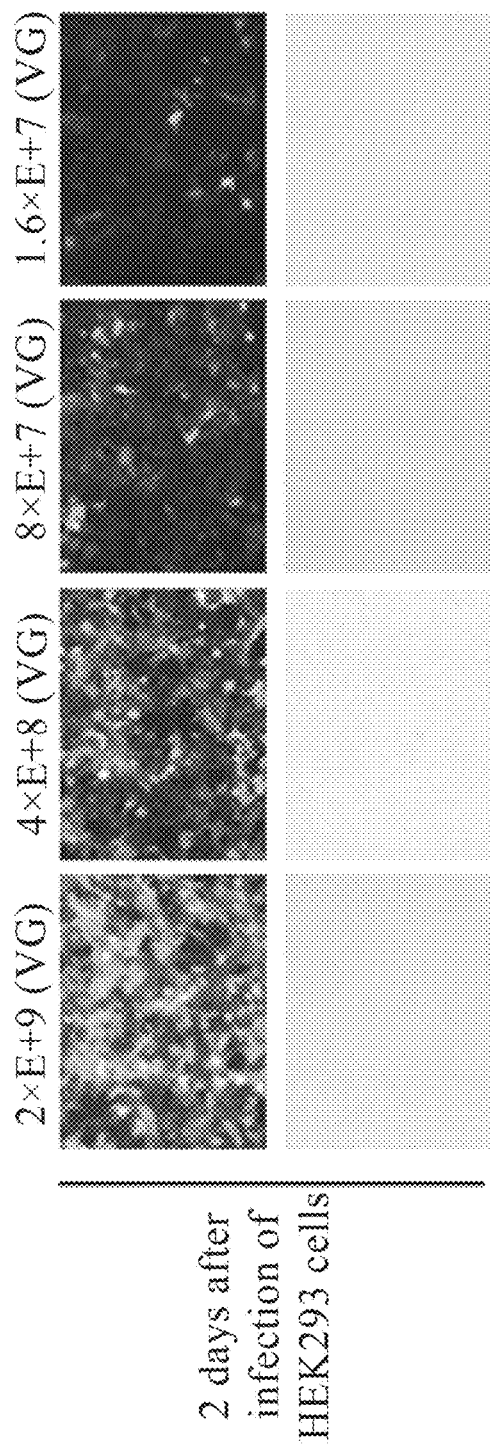
FIG. 5 is fluorescence microscopy images of a purified rAAV-infected HEK293 cell in Example 2.

HEK293 cells were seeded into 96-well plates at $1 \times 10^4$ cells/well and were infected with the purified rAAV of corresponding concentration gradient. 48 h after infection, the expression of GFP was observed by fluorescence microscopy, as shown in FIG. 5. The results show that rAAV prepared by the method of the invention has good cell-level transduction activity.

Example 3

Preparation of rAAV by Infecting Sf9/Cap Packaging Cell Lines With Recombinant BEV/Rep-(ITR-GFP)

(1) The corresponding host packaging cell line was infected with the recombinant baculovirus in which the rAAV genome ITR-GFP and the Rep gene were integrated.

The recombinant baculovirus, i.e., recombinant BEV/Rep-(ITR-GFP), integrated with the rAAV genome ITR-GFP and the Rep gene, was prepared and amplified as follows:

To place the ITR-GFP and the Rep gene in a recombinant baculovirus, pFast. Bac. Dual (pFBD) shuttle vector was used (FIG. 1B). In the example, the Rep gene of the serotype 2 AAV was codon optimized based on the ribosomal leaky scanning principle and the Rep gene was placed under the control of the P10 promoter (FIG. 2C) or the control of the PH promoter (FIG. 2D), under which the functional expression of the Rep gene is achieved. The Rep gene sequence is SEQ ID No. 6 or SEQ ID No. 7 (RepA or RepB). The ITR-GFP is nucleic acid sequence of type 2 AAV, i.e., the sequence of SEQ ID No. 3, and contains an expression cassette of GFP. CMV promoter controls the expression of GFP so as to allow for easy detection of the recombinant virus activity. The ITR-GFP is linked to the Rep gene expression cassette or the vector via a 5' terminal ligation nucleic acid fragment or a 3' terminal ligation nucleic acid fragment. The 5' terminal ligation nucleic acid fragment or the 3' terminal ligation nucleic acid fragment is a sequence of SEQ ID No. 4 (link A) or SEQ ID No. 5 (link B).

In this example, the recombinant baculovirus may have one of the structures as follows:

RepA-LinkA-(ITR-GFP)-linkB

A recombinant shuttle plasmid pFBD/Rep-(ITR-GFP) was constructed by placing the ITR-GFP on one side of the pFBD/Rep vector via a ligation nucleic acid fragment using conventional molecular cloning techniques.

The recombinant shuttle plasmid was transformed into DH10Bac containing the AcMNPV baculovirus genome according to the Bac-to-Bac system protocol. Recombinant baculovirus genome (Bacmid) was obtained by Tn7 transposon element-mediated recombination. Positive bacteria containing recombinant Bacmid were obtained by blue-white screening and PCR identification. Recombinant Bacmid was extracted and purified and transfected into adherently cultured Sf9 cells. Sf9 cells were completely infected with recombinant baculovirus and showed obvious cytopathic effect (CPE). The cell culture was centrifuged at 3000 rpm for 5 min, and the resulting recombinant baculovirus was contained in the supernatant.

The supernatant was used to infect adherently cultured Sf9 cells and cultured for 3 days. The control group of uninfected Sf9 cells were in the normal state without GFP expression, while the Sf9 cells infected with the recombinant BEV/Rep-(ITR-GFP) had a significant CPE phenomenon and obvious GFP expression, as the results shown in FIG. 6A. Three days after infection, the cell culture supernatant was centrifuged at 3000 rpm for 5 min, and the BEV supernatant was obtained. The titer of the BEV was determined by the method of fluorescent quantitative PCR. See, Proc Natl Acad Sci USA, 2009. 106 (13): 5059-64.

Figure 6A:
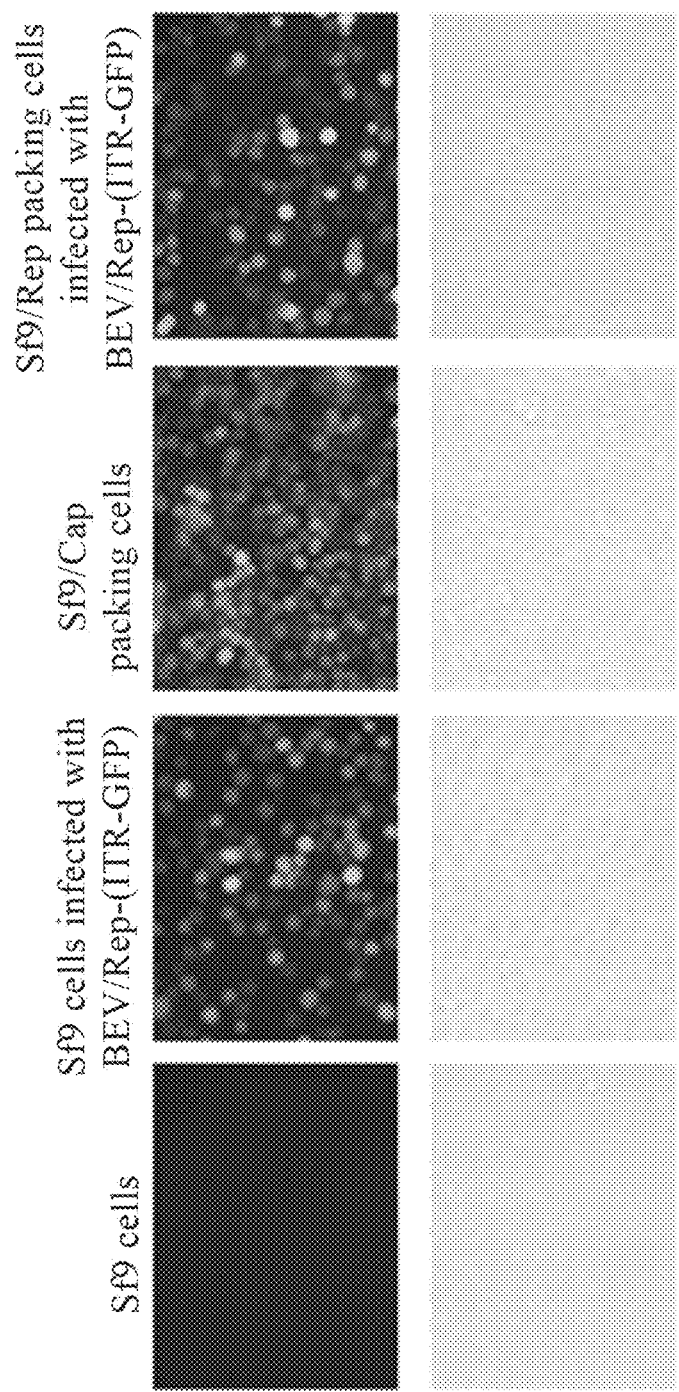
FIG. 6A is fluorescence microscopy images of Sf9 cells and Sf9/Cap packing cells uninfected or infected with recombinant baculovirus BEV/Rep-(ITR-GFP) in Example 3.

The corresponding host packaging cell line, i.e., the Sf9/Cap packaging cell line that inducible expression of the Cap gene, was established as follows:

To facilitate the screening of packaging cell lines, the existing pIR-VP-hr2-RBE plasmid (see, Proc Natl Acad Sci USA, 2009. Mar. 31; 106 (13): 5059-64) was modified: the C-terminus of the blasticidin (Bsd) gene was fused to the GFP gene by FMDV self-cleaving polypeptide 2A to obtain the pIR-VP-hr2-RBE-bsd-GFP plasmid (FIG. 2F). Then, the modified plasmid was transfected into Sf9 cells, and the Sf9/Cap packaging cell line integrated with the Cap gene expression cassette was obtained by Bsd antibiotic screening. This cell line constitutively expresses GFP and can be further isolated by monoclonal isolation or by flow cytometry to obtain the Sf9/Cap packaging cell line with a high yield of rAAV, as shown in FIG. 6A.

(2) rAAV was produced via infecting Sf9/Cap cell lines with BEV/Rep-(ITR-GFP) and its activity was verified.

The suspended Sf9/Rep cell lines were infected with BEV/Rep-(ITR-GFP) at MOI=5. Three days after infection, the cell culture was centrifuged at 3000 rpm for 5 minutes to collect the culture supernatant and the cell pellet. The BEV was mainly released by secretion into the medium supernatant, and some of the non-released BEV was also existed in Sf9/Cap cells. The rAAV was mainly existed in the nuclei of Sf9/Cap cells and some rAAV was released into the supernatant because of CPE, as shown in FIG. 6A. As a result, BEV and rAAV were existed in both supernatants and cell pellets.

Figure 6B:
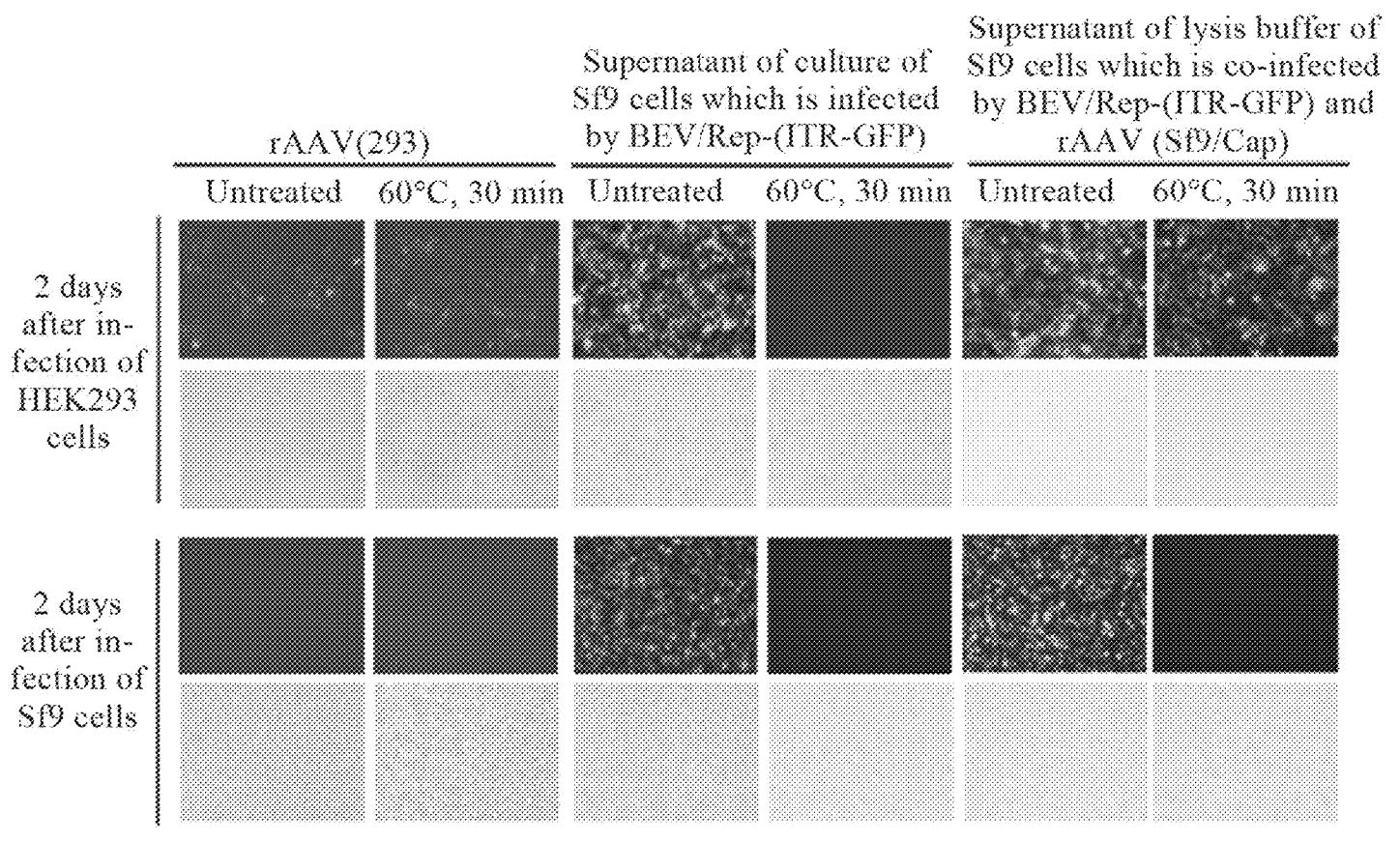

In order to verify the production of rAAV by infecting Sf9/Cap cells with the BEV/Rep-(ITR-GFP) we use a simple HEK293 cells and Sf9 cells-based infection assay to test the AAV activity. The experimental results are shown in FIG. 6B. The detailed process and the results are as follows: The cell pellet were lysed by freeze-thaw using liquid nitrogen and a 37° C. water bath for three times, then centrifuged at 5000 rpm for 5 min and supernatant of cell lysis was collected. Because rAAV was enveloped, its activity was not affected by heating at 60° C. for 30 minutes, whereas recombinant baculovirus (BEV) was enveloped and lost its activity after treatment at 60° C. for 30 minutes. For rAAV2 (293 cells derived) samples, in 293 cells-based infection assays, both the treated and untreated can express GFP. In Sf9 cells-based infection assays, both the treated and untreated cannot express GFP. It indicates that rAAV2 do not infect Sf9 cells. For BEV/Rep-(ITR-GFP) samples, both in 293 cells and Sf9 cells-based infection assays, only the untreated can express GFP, while the treated cannot express GFP. For the BEV/Rep-(ITR-GFP) infected Sf9/Cap cell lysate supernatant samples, which contain some non-secrete BEVs and the major rAAV. In 293 cells-based infection assays, both the treated and untreated can express GFP, but the treated expressing GFP decrease slightly. It indicates that there are a lot of rAAV2 expressing GFP. In Sf9 cells-based infection assays, the untreated can express GFP, while the treated cannot express GFP.

(3) The recombinant adeno-associated virus obtained in (2) was isolated and purified.

Purification, titer determination and cell-level transduction activity validation of rAAV:

About $1\times10^8$ Sf9/Cap cells were collected after recombinant BEV infection. After adding 10 ml of lysis buffer (50 mM Tris-Cl, 150 mM NaCl, 2 mM $MgCl_2$, pH 8.0), the cell pellets were lysed by freeze-thaw using liquid nitrogen and a 37° C. water bath for three times, and then centrifuged at 5000 rpm for 5 min. The supernatant was collected, and nuclease Benzonase was added to the supernatant to a final concentration of 50 U/ml. The mixture was incubated in water bath at 37° C. for 60 min. After centrifugation at 5000 rpm for 10 min, the supernatant was collected. The supernatant was extracted with chloroform and the extracted supernatant was further purified by two-phase precipitation with a solution containing 13.2% $(NH_4)_2SO_4$ and 10% PEG8000 (J Virol Methods, 2007. 139 (1): 61-70, J Virol Methods, 2012. 179 (1): 276-80). The two-phase precipitated supernatant was dialyzed and desalted with a PBS solution and concentrated to a final volume of 1 ml by an Amicon ultra-4 (100 kD cutoff) dialysis column and stored at −80° C. after aseptic aliquots. The titer of rAAV was determined by fluorescence quantitative PCR, and the titer unit was expressed as VG/ml.

The rAAV yield of the purification process is shown in Table 3. The experimental results showed that the yield of rAAV reaches $6.84\times10^4$ VG in a single Sf9/Cap cell, and the recovery rate reaches 28.8% after purification by this method.

TABLE 3 rAAV purification process yield analysis

| Purification step | Volume (mL) | rAAV concentration (VG/mL) | rAAV amount (VG) | rAAV yield (%) |
|---|---|---|---|---|
| Lysate treated supernatant | 20 | $3.42 \times 10^{11}$ | $6.84 \times 10^{12}$ | 100 |
| Chloroform treated supernatant | 20 | $2.85 \times 10^{11}$ | $5.70 \times 10^{12}$ | 83.3 |
| two-phase precipitated supernatant | 27 | $1.76 \times 10^{11}$ | $4.75 \times 10^{13}$ | 69.4 |
| Dialysis treated supernatant | 1 | $1.97 \times 10^{12}$ | $1.97 \times 10^{12}$ | 28.8 |

Figure 6C:
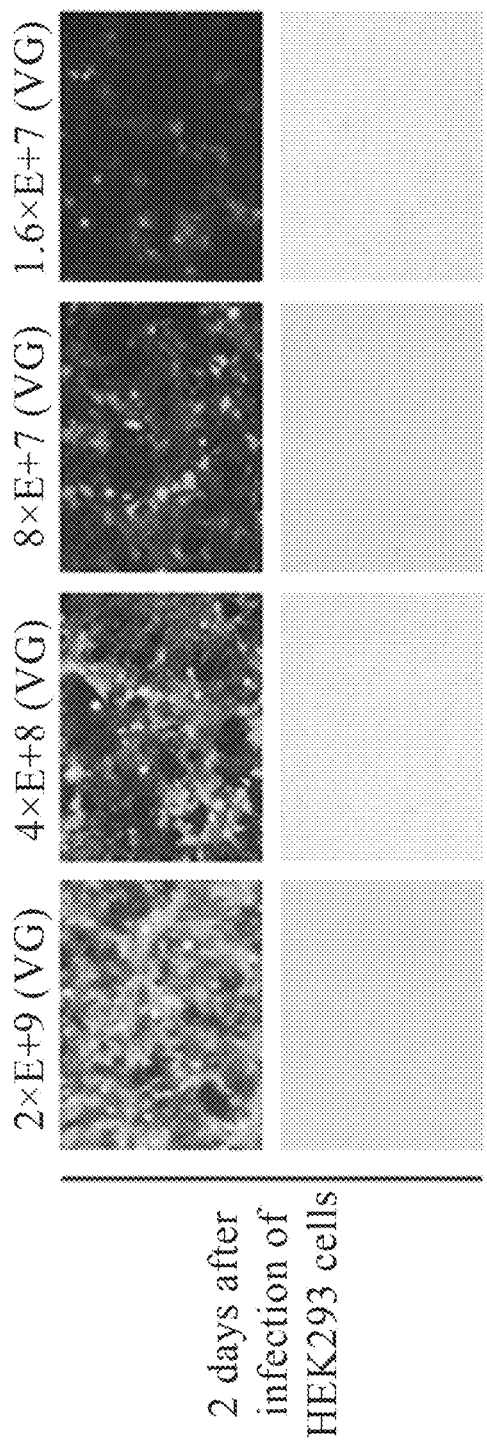
FIG. 6C is fluorescence microscopy images of a purified rAAV-infected HEK293 cell in Example 3.

HEK293 cells were seeded into 96-well plates at $1\times10^4$ cells/well and were infected with the purified rAAV of corresponding concentration gradient. 48 h after infection, fluorescence microscopy was used to observe the expression of GFP, as shown in FIG. 6C. The results show that rAAV prepared by the method of the invention has good cell-level transduction activity.

Example 4

Preparation of rAAV by Infection of Sf9/Cap Packaging Cell Lines With Recombinant BEV/Rep-(ITR-GFP)

This example is similar to example 3 except for that the recombinant baculovirus has the following main components:

LinkA-(ITR-GFP)-linkB-RepB

After infection of the recombinant BEV/Rep-(ITR-GFP) in this example with the Sf9/Cap packaging cell line, the prepared rAAV was purified. The rAAV yield of the purification process is shown in Table 4. The experimental results show that the yield of rAAV in a single Sf9/Cap packaging cell was up to $8.16\times10^4$ VG. After the purification, the recovery rate reached 34.7%.

TABLE 4 rAAV purification process yield analysis

| Purification step | Volume (mL) | rAAV concentration (VG/mL) | rAAV amount (VG) | rAAV yield (%) |
|---|---|---|---|---|
| Lysate treated supernatant | 20 | $4.08 \times 10^{11}$ | $8.16 \times 10^{12}$ | 100 |
| Chloroform treated supernatant | 20 | $3.28 \times 10^{11}$ | $6.36 \times 10^{12}$ | 77.9 |
| two-phase precipitated supernatant | 27 | $1.97 \times 10^{11}$ | $5.32 \times 10^{13}$ | 65.2 |
| Dialysis treated supernatant | 1 | $2.83 \times 10^{12}$ | $2.83 \times 10^{12}$ | 34.7 |

Figure 7:
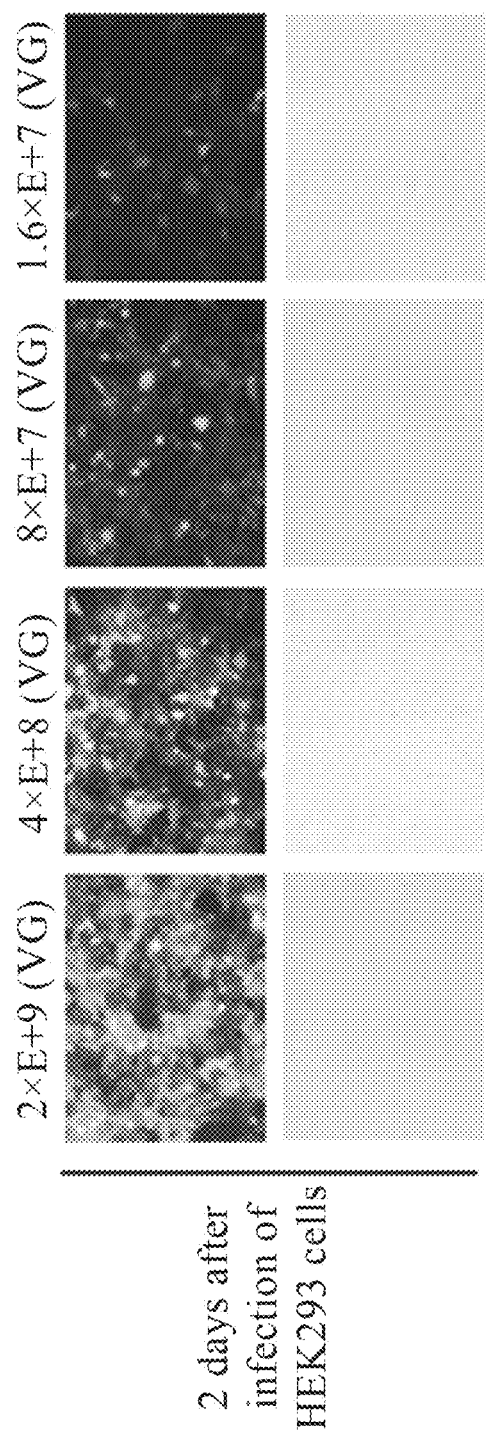
FIG. 7 is fluorescence microscopy images of the purified rAAV-infected HEK293 cells prepared in Example 4.

HEK293 cells were seeded into 96-well plates at $1\times10^4$ cells/well and were infected with the purified rAAV of corresponding concentration gradient. 48 h after infection, fluorescence microscopy was used to observe the expression of GFP, as shown in FIG. 7. The results show that rAAV prepared by the method of the invention has good cell-level transduction activity.

Unless otherwise indicated, the numerical ranges involved in the invention include the end values. While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for producing a recombinant adeno-associated virus (rAAV), the method comprising:
   (1) infecting a host packaging cell line with a recombinant baculovirus in which a rAAV genome ITR-GOI (gene of interest) and a first gene are integrated, wherein the first gene is selected from an AAV Cap gene or an AAV Rep gene, the ITR-GOI is linked to the first gene via a 5' terminal ligation nucleic acid fragment or a 3' terminal ligation nucleic acid fragment, and the 5' terminal ligation nucleic acid fragment and the 3' terminal ligation nucleic acid fragment are ligation nucleic acid sequence having a length ranging from 81 to 140 bp;
   wherein a genome of the host packaging cell line is integrated with a second gene expression cassette that induces expression of a second gene, the second gene is selected from the AAV Cap gene or the AAV Rep gene, and the host packaging cell line is used for facilitating the replication and assembly of rAAV,
   wherein the recombinant baculovirus is constructed by using a shuttle vector and the following steps:
      a. the shuttle vector comprises a P10 promoter, an intermediate sequence and a PH promoter, the rAAV genome ITR-GOI is cloned into the intermediate sequence between the P10 promoter and the PH promoter of the shuttle vector; and
      b. the first gene is cloned into a multiple cloning site downstream of the P10 promoter or the PH promoter of the shuttle vector, wherein the second gene is the AAV Rep gene when the first gene is the AAV Cap gene, or the second gene is the AAV Cap gene when the first gene is the AAV Rep gene;
   (2) culturing the host packaging cell line infected with recombinant baculovirus in (1) to produce the rAAV; and
   (3) isolating and purifying the rAAV obtained in (2).

2. The method of claim 1, wherein the recombinant baculovirus in which a rAAV genome ITR-GOI and an AAV Cap gene or an AAV Rep gene are integrated carries a gene of interest (GOI) flanked by the AAV inverted terminal repeats (ITR).

3. A recombinant baculovirus, wherein a genome of the recombinant baculovirus contains a rAAV ITR-GOI and a Cap gene of a corresponding serotype, and the recombinant baculovirus is used to provide the ITR-GOI and the Cap gene required for rAAV production,
   wherein the recombinant baculovirus is constructed by using a shuttle vector and the following steps:
      a. the shuttle vector comprises a P10 promoter, an intermediate sequence and a PH promoter, the rAAV genome ITR-GOI is cloned into the intermediate sequence between the P10 promoter and the PH promoter of the shuttle vector; and
      b. the Cap gene is cloned into a multiple cloning site downstream of the P10 promoter or the PH promoter of the shuttle vector to obtain a corresponding shuttle plasmid,
   the ITR-GOI is linked to the Cap gene via a 5' terminal ligation nucleic acid fragment or a 3' terminal ligation nucleic acid fragment, and the 5' terminal ligation nucleic acid fragment and the 3' terminal ligation nucleic acid fragment are ligation nucleic acid sequence having a length ranging from 81 to 140 bp.

4. The recombinant baculovirus of claim 3, wherein a sequence of the Cap gene is a codon-optimized sequence according to a principle of ribosomal leaky scanning.

5. A recombinant baculovirus, wherein a genome of the recombinant baculovirus contains a rAAV ITR-GOI and a Rep gene of a corresponding serotype, and the recombinant baculovirus is used to provide the ITR-GOI and the Rep gene required for rAAV production,
   wherein the recombinant baculovirus is constructed by using a shuttle vector and the following steps:
      a. the shuttle vector comprises a P10 promoter, an intermediate sequence and a PH promoter, the rAAV genome ITR-GOI is cloned into the intermediate sequence between the P10 promoter and the PH promoter of the shuttle vector; and
      b. the Rep gene is cloned into a multiple cloning site downstream of the P10 promoter or the PH promoter of the shuttle vector to obtain a corresponding shuttle plasmid,
   the ITR-GOI is linked to the Rep gene via a 5' terminal ligation nucleic acid fragment or a 3' terminal ligation nucleic acid fragment, and the 5' terminal ligation nucleic acid fragment and the 3' terminal ligation nucleic acid fragment are ligation nucleic acid sequence having a length ranging from 81 to 140 bp.

6. The recombinant baculovirus of claim 5, wherein a sequence of the Rep gene is a codon-optimized sequence according to a principle of ribosomal leaky scanning.

7. The method of claim 1, wherein the 5' terminal ligation nucleic acid fragment and the 3' terminal ligation nucleic acid fragment are ligation nucleic acid sequence having the length of 81 bp.

8. The method of claim 1, wherein the 5' terminal ligation nucleic acid fragment and the 3' terminal ligation nucleic acid fragment are ligation nucleic acid sequence having the length of 140 bp.

9. The recombinant baculovirus of claim 3, wherein the 5' terminal ligation nucleic acid fragment and the 3' terminal ligation nucleic acid fragment are ligation nucleic acid sequence having the length of 81 bp.

10. The recombinant baculovirus of claim 3, wherein the 5' terminal ligation nucleic acid fragment and the 3' terminal ligation nucleic acid fragment are ligation nucleic acid sequence having the length of 140 bp.

11. The recombinant baculovirus of claim 5, wherein the 5' terminal ligation nucleic acid fragment and the 3' terminal ligation nucleic acid fragment are ligation nucleic acid sequence having the length of 81 bp.

12. The recombinant baculovirus of claim 5, wherein the 5' terminal ligation nucleic acid fragment and the 3' terminal ligation nucleic acid fragment are ligation nucleic acid sequence having the length of 140 bp.

* * * * *

SEQUENCE LISTING

<160> NUMBER OF SEQ ID NOS: 10

<210> SEQ ID NO 1
<211> LENGTH: 2208
<212> TYPE: DNA
<213> ORGANISM: Artificial Sequence
<220> FEATURE:
<223> OTHER INFORMATION: Fully synthetic

<400> SEQUENCE: 1

| | | | | | |
|---|---|---|---|---|---|
| acggctgccg | acggttacct | acccgactgg | ctcgaagaca | ctctgtctga | aggtataaga | 60 |
| cagtggtgga | agctcaagcc | tggcccaccg | ccaccaaagc | ctgcagagcg | gcataaggac | 120 |
| gacagcagag | gtcttgtgct | acctgggtac | aagtacctcg | gacccttcaa | cgggctcgac | 180 |
| aagggcgagc | cggtcaacga | ggcagacgcc | gcggcccctcg | agcacgacaa | agcgtacgac | 240 |
| cggcagctcg | acagcggaga | caatccgtac | ctcaaataca | accacgccga | cgcggagttt | 300 |
| caggagcgcc | ttaaagaaga | tacgtctttt | ggggggcaacc | tcggacgagc | agtcttccaa | 360 |
| gcgaagaaga | gggttcttga | acctctgggc | ctggtcgagg | aacctgttaa | gacggctccg | 420 |
| ggaaaaaaga | ggccggtaga | acactcccct | gtggagccag | actcctcctc | gggaacagga | 480 |
| aaggcgggtc | agcagcctgc | aagaaaaaga | ttgaattttg | gtcagactgg | agacgcagat | 540 |
| tcagtgcctg | accccagcc | tctcggacag | ccgccagcag | caccctctgg | tctgggaact | 600 |
| aatacgatgg | ctacaggcag | tggcgcacca | atggcagaca | taacgaggg | cgccgacgga | 660 |
| gtgggtaatt | catcgggaaa | ttggcattgc | gattccacgt | ggatgggaga | cagagtcatc | 720 |
| accaccagca | cccgaacctg | ggccctgccc | acctacaaca | accacctcta | caagcaaatt | 780 |
| tcgagccaat | caggagcctc | gaacgataat | cactacttcg | gctacagcac | cccttggggg | 840 |
| tattttgatt | tcaacaggtt | ccactgccac | ttttcaccac | gtgactggca | gagactcatc | 900 |
| aataacaact | ggggattccg | acccaagaga | ctcaacttca | agctctttaa | cattcaagtc | 960 |
| aaggaggtca | cgcagaatga | cggtacgacg | acgattgcca | ataatcttac | cagcacggtt | 1020 |
| caggtgttta | ctgactcgga | gtaccagctc | ccgtacgtcc | tcgactcggc | gcatcaagga | 1080 |
| tgcctcccgc | cgtttccagc | agacgtattc | atggtgccac | agtatggata | cctcaccctg | 1140 |
| aacaacggga | gtcaggcagt | gggacgctct | tcattttact | gcctggagta | cttgccttct | 1200 |
| cagatgctgc | gtaccggaaa | caactttacc | ttcagctaca | cttttgagga | cgtccctttc | 1260 |
| cacagcagtt | acgctcacag | ccagagtctg | gaccgtctca | tgaatccact | catcgatcag | 1320 |
| tacctgtatt | acttgagcag | aacaaacact | ccaagtggaa | caaccacgca | gtcaaggctt | 1380 |
| cagttctctc | aggcaggagc | gagtgacatt | cgggaccagt | ctaggaactg | gcttcctgga | 1440 |
| ccctgttacc | gccagcagcg | agtttcaaaa | acatctgcgg | ataacaacaa | cagtgagtac | 1500 |
| tcttggactg | gagctaccaa | gtaccacctc | aatggcagag | actctctggt | gaatccgggc | 1560 |
| ccggctatgg | caagtcacaa | ggacgatgaa | gaaaagtttt | tccctcaaag | cggagttctc | 1620 |
| atctttggga | agcaaggctc | agagaaaaca | aatgtagaca | tcgaaaaggt | catgattaca | 1680 |
| gacgaagagg | aaatcagaac | aacaaatccc | gtggctacgg | agcagtatgg | ttctgtatct | 1740 |
| accaacctcc | agagaggcaa | cagacaagcg | gctacagcag | atgtcaacac | acaaggcgtt | 1800 |
| cttccaggca | tggtttggca | cgacagagat | gtgtaccttc | aggggcccat | ctgggcaaaa | 1860 |
| attccgcaca | cggacggaca | ttttcacccc | tctccactca | tgggaggatt | cggacttaaa | 1920 |
| cacccctctc | cacagattct | catcaagaac | acccccgtac | ctgcaaatcc | ttcgacgacc | 1980 |
| ttcagtgcgg | caaagtttgc | ttccttcatc | acgcagtact | caacgggaca | ggtcagcgtg | 2040 |

| | |
|---|---|
| gagatcgagt gggagctgca gaaggagaac agcaagcgct ggaatcccga aattcagtac | 2100 |
| acctccaact ataacaagtc tgtcaatgtg gacttcactg tggacactaa tggcgtgtat | 2160 |
| tcagagccac gccccatagg caccagatat ctgactcgca atctgtaa | 2208 |

<210> SEQ ID NO 2
<211> LENGTH: 2208
<212> TYPE: DNA
<213> ORGANISM: Artificial Sequence
<220> FEATURE:
<223> OTHER INFORMATION: Fully synthetic

<400> SEQUENCE: 2

| | |
|---|---|
| acggctgccg acggttacct acccgactgg ctcgaagaca ctctgtctga aggtataaga | 60 |
| cagtggtgga agctcaagcc tggcccaccg ccaccaaagc ctgcagagcg gcataaggac | 120 |
| gacagcagag gtcttgtgct acctgggtac aaatacctcg gacccttcaa cgggctcgac | 180 |
| aagggcgagc cggtcaacga ggcagacgcc gcggccctcg agcacgacaa agcgtacgac | 240 |
| cggcagctag acagcggaga caatccgtac ctcaaatcca ccacgccga cgcggagttt | 300 |
| caggagcgcc ttaaagaaga tacgtctttt ggggcaacc tcggacgagc agtcttccaa | 360 |
| gcgaagaaga gggttcttga gcctctgggc ctggttgagg aacctgttaa gacggctccg | 420 |
| ggaaaaaaga ggccggtaga gcactctcct gtggagccgg actcctcttc gggaaccgga | 480 |
| aaggcgggcc agcagcctgc aagaaaaaga ttgaattttg gtcagactgg agacgcagac | 540 |
| tcagtacctg acccacagcc tctgggacag ccaccagcag cccctctgg tctgggaact | 600 |
| aatacgatgg ctacaggcag tggcgcacca atggcagaca taacgagggcgccgacgga | 660 |
| gtgggtaatt cctcgggaaa ctggcattgt gattccacat ggatgggcga cagagtcatc | 720 |
| accaccagca cccgaacctg ggccctgccc acctacaaca accacctcta caaacaaatt | 780 |
| tcaagccaat caggtgcctc gaatgacaat cactactttg gctacagcac cccttggggg | 840 |
| tattttgact tcaacaggtt ccactgccac ttctcaccgc gtgactggca agactcatc | 900 |
| aacaacaact ggggattccg acccaagaga ctcaacttca gctctttaa cattcaagtc | 960 |
| aaagaggtca cacagaatga tggtacgacg acgattgcca ataaccttac cagcacggtt | 1020 |
| caggtgttta ctgactcgga gtaccagctc ccgtacgtcc tcggctcggc gcgtcaagga | 1080 |
| tgtctcccgc cgttcccagc agacgtcttc atggtgccac agtatggata cctcaccctg | 1140 |
| aacaacggga gtcaggcagt aggacgctct tcattctact gtctggagta ctttccttct | 1200 |
| cagatgctgc gtaccggaaa caactttacc ttcagctaca cttttgagga cgttcctttc | 1260 |
| cacagcagct acgctcacag ccaaagtcta gaccgtctca tgaatcctct catcgaccag | 1320 |
| tacctgtatt acttgagcag aacaaacact ccaagtggaa ccaccacgca gtcaagactt | 1380 |
| cagttctctc aggccggagc gagtgacatt cgggaccagt ctaggaactg gcttcctgga | 1440 |
| ccctgttacc gccagcagcg agtatcaaag acatctgcgg ataataacaa cagtgagtac | 1500 |
| tcgtggactg gagctaccaa gtaccacctc aatggcagag actctctggt gaatccgggc | 1560 |
| ccggccatgg caagccataa ggacgatgaa gagaaattct ttcctcagag cggggttctc | 1620 |
| atctttggga agcaaggctc agagaaaaca aatgtggaca ttgaaaaggt catgatcaca | 1680 |
| gacgaagaag aaatcaggac aaccaatccc gtggctacgg agcagtatgg ttctgtatct | 1740 |
| accaacctcc agagaggcaa cagacaagca gctaccgcag atgtcaatac acaaggcgtc | 1800 |
| cttccaggta tggtctggca ggacagagat gtgtaccttc aggggccat ctgggcaaag | 1860 |
| attccacaca cggacggaca tttccaccca tctccactca tgggtggatt tggacttaaa | 1920 |

```
catcctcctc cacagattct catcaagaac accccggtac ctgcgaatcc ttcgaccacc    1980
ttcagtgcag caaagttcgc ttccttcatc acacagtact ccacgggaca ggtcagcgtg    2040
gagatcgagt gggagctgca aaggagaac agcaaacgct ggaaccccga gattcagtac     2100
acttccaact acaacaagtc tgttaatgtg gactttactg tggacactaa tggagtgtat    2160
tcagaacctc gcccaattgg cacgagatac ctcactcgta atctgtaa                 2208

<210> SEQ ID NO 3
<211> LENGTH: 141
<212> TYPE: DNA
<213> ORGANISM: Artificial Sequence
<220> FEATURE:
<223> OTHER INFORMATION: Fully synthetic

<400> SEQUENCE: 3
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc t                                              141

<210> SEQ ID NO 4
<211> LENGTH: 140
<212> TYPE: DNA
<213> ORGANISM: Artificial Sequence
<220> FEATURE:
<223> OTHER INFORMATION: Fully synthetic

<400> SEQUENCE: 4
tacagctcga tatactgcgg aagtctgatc tgagcatcga ttattgtcta gctcgtcaga     60
ggcgctgaac ctatcgataa actccagaaa tgcagcctat taaccgttgc tagcctattg    120
cacgccttca gctgtcatgt                                                140

<210> SEQ ID NO 5
<211> LENGTH: 81
<212> TYPE: DNA
<213> ORGANISM: Artificial Sequence
<220> FEATURE:
<223> OTHER INFORMATION: Fully synthetic

<400> SEQUENCE: 5
gcggctcgat cgcgtattat ctagttaccg atctgaccgg aatatcacag cgcactcgtc     60
tcagcatcga tactgactac t                                               81

<210> SEQ ID NO 6
<211> LENGTH: 1866
<212> TYPE: DNA
<213> ORGANISM: Artificial Sequence
<220> FEATURE:
<223> OTHER INFORMATION: Fully synthetic

<400> SEQUENCE: 6
ctggcggggt tctacgaaat tgtcattaag gtcccaagcg acctggacgg gcatctgccc     60
ggcatttccg acagcttcgt gaactgggtg gccgagcagg agtgggagtt accgccagat    120
tctgacttag atctgaatct aattgagcag gcgcccctga ctgtggccga gaagctgcag    180
cgcgactttc taacggagtg gcgccgtgtg agtaaggccc cggaggccct tttctttgtg    240
caatttgaca agggagagag ctatttccac ttcacgtgc tagtggaaac caccggggtg     300
aaatccttag ttttgggacg tttcctgagt cagattcgcg aaaaactgat tcagaggatt    360
taccgcggga tcgagccgac tttgccgaac tggttcgcgg tcacaaagac cagaaacggt    420
```

```
gccggaggcg ggaacaaggt ggtcgacgag tgctacatcc ccaattattt gctcccgaaa       480
acccagcctg agctccagtg ggcctggact aatttcgaac agtacttaag cgcctgtttg       540
aatctcacgg agcgtaaacg gttggtggcg cagcatctga cgcacgtgtc gcagacgcag       600
gatcagaaca agagaatca gaatcccaat tctgacgcgc cggtgatcag atcaaaaacg        660
tcagccaggt acatggagct agtcgggtgg ctcgtggata aggggattac ctcggagaag       720
cactggatcc aggaggacca ggcttcatac atctccttca atgcggcctc caagtcgcgg       780
tcccaaatca aggctgcgtt ggacaatgcg ggtaagatta tgagcctgac taaaaccgcc       840
cccgactatc tggtgggcca gcagcccgtg aagacattt ccagcaatcg gatttataaa       900
attttggagc taaacgggta cgatccccaa tatgctgctt cagtcttttct gggatgggcc      960 acgaaaaagt tcggcaagag gaacaccatc tggctgtttg ccctgcaac taccgggaag      1020 accaacatcg cagaggcaat agcccacact gtgcccttct acgggtgcgt aaactggacg      1080
aatgagaact tccccttcaa cgactgtgtc gacaaaatgg tgatctggtg gaagagggg      1140 aagatgaccg ccaaggtcgt ggagtcggcc aaagcgattc taggaggaag caaggtgcgc      1200
gtggaccaga agtgcaagtc gtcggcccag atagatccga ctcccgtgat cgtcacctcg      1260
aacacgaaca tgtgcgccgt gattgacggc aactcaacga cgttcgaaca ccagcagccg      1320
ttgcaggacc gtatgttcaa atttgaactc acccgccgtc tcgatcatga cttcgggaag      1380
gtcaccaagc aggaagtcaa ggacttcttc cggtgggcaa aggatcacgt ggttgacgtg      1440
gagcacgaat tctacgtcaa aaagggtgga gccaagaaga gaccagcccc cagtgacgca      1500
gatataagcg agccaaagcg ggtgcgagag tcagttgcgc agccatcgac gtcagacgcg      1560
aaagcttcga taaactacgc ggacaggtac caaaacaaat gttctcgaca cgtcggcatg      1620
aatctaatgc tgttccctctg cagacaatgc gagaggatga atcaaaattc gaatatctgt      1680
ttcactcacg gacagaaaga ctgtttggag tgcttgcccg tgtcagagtc tcaacctgtt      1740
tctgtcgtca agaaggcgta tcagaagctg tgctacattc atcatatcat gggcaaggtg      1800
ccggacgctt gcactgcgtg cgacctggtc aatgtagatt tggacgactg catcttcgaa      1860
caataa                                                                   1866
```

<210> SEQ ID NO 7
<211> LENGTH: 1866
<212> TYPE: DNA
<213> ORGANISM: Artificial Sequence
<220> FEATURE:
<223> OTHER INFORMATION: Fully synthetic

<400> SEQUENCE: 7

```
ctggcgggt tctacgaaat tgtcattaag gtcccaagcg acctggacgg gcatctgccc        60
ggcatttctg acagcttcgt gaactgggtg gccgagcagg agtgggagtt gccgccagat       120
tctgacttag atctgaatct gattgagcag gcgcccctga ctgtggccga gaagctgcag       180
cgcgactttc taacggagtg gcgccgtgtg agtaaggccc cggaggccct tttctttgtg       240
caatttgaca agggagagag ctacttccac ttacacgtgc tagtggaaac caccggggtg       300
aaatccttag ttttgggacg tttcctgagt cagattcgcg aaaaactgat tcagaggatt       360
taccgcggga tcgagccgac tttgccgaac tggttcgcgg tcacaaagac cagaaacggt       420
gccggaggcg ggaacaaggt ggtggacgag tgctacatcc ccaattactt gctcccaaa       480 acccagcctg agctccagtg ggcgtggact aatttagaac agtatttaag cgcctgtttg       540
aatctcacgg agcgtaaacg gttggtggcg cagcatctga cgcacgtgtc gcagacgcag       600
```

-continued

```
gagcagaaca aagagaatca gaatcccaat tctgacgcgc cggtgatcag atcaaaaact    660
tcagccaggt acatggagct agtcgggtgg ctcgtggata agggattac ctcggagaag    720 cactggatcc aggaggacca ggcttcatac atctccttca atgcggcctc caagtcgcgg    780
tcccaaatca aggctgcgtt ggacaatgcg ggtaagatta tgagcctgac taaaaccgcc    840
cccgactatc tggtgggcca gcagcccgtg aagacatttt ccagcaatcg gatttataaa    900
attttggagc taaacggcta cgacccacaa tatgcggctt ccgtctttct gggatgggcc    960
acgaaaaagt tcggcaagag gaacaccatc tggctgtttg ggcctgcgac tacagggaaa   1020
accaatatcg cggaggccat agcccacact gtgcccttct acgggtgcgt aaactggacc   1080
aatgagaact ttcccttcaa cgattgtgta gacaaaatgg tgatctggtg ggaggagggg   1140
aagatgaccg ccaaggtcgt ggagtcggcc aaagccattc tcggaggaag caaggtacgc   1200
gtggaccaga aatgcaagtc ctcggcccag atagacccga ctcccgtgat cgtcacctcc   1260
aacaccaaca tgtgtgccgt aattgacggc aactcaacga ccttcgaaca ccagcagccg   1320
ttgcaagacc ggatgttcaa gtttgaactc actcgccgtc tggatcatga ctttgggaag   1380
gtcaccaagc aggaagtcaa agactttttc cggtgggcaa aagatcacgt ggtcgaggtg   1440
gagcatgaat tctacgtcaa aaagggtgga gccaagaaaa gacccgctcc cagtgatgca   1500
gatataagcg agcccaaacg ggtgcgcgag tcagttgcgc agccatcgac gtcagacgcg   1560
gaagcttcga tcaactacgc agacaggtac cagaacaagt gttctcgtca tgtgggcatg   1620
aatctgatgc tgtttccctg cagacaatgc gagagaatga atcagaattc aaatatctgt   1680
ttcactcacg ggcagaagga ctgtttagag tgctttcccg tgtcagaatc tcaacccgtt   1740
tctgtcgtca aaaaggcgta tcagaaactg tgctatattc atcatataat gggcaaggtg   1800
ccagacgctt gcactgcctg cgatctggtc aatgtggatt tggacgactg catcttggaa   1860
caataa                                                               1866
```

<210> SEQ ID NO 8
<211> LENGTH: 122
<212> TYPE: DNA
<213> ORGANISM: Artificial Sequence
<220> FEATURE:
<223> OTHER INFORMATION: Fully synthetic

<400> SEQUENCE: 8

```
atacggacct ttaattcaac ccaacacaat atattatagt taaataagaa ttattatcaa     60
atcatttgta tattaattaa aatactatac tgtaaattac attttattta caatcactcg    120
ac                                                                    122
```

<210> SEQ ID NO 9
<211> LENGTH: 128
<212> TYPE: DNA
<213> ORGANISM: Artificial Sequence
<220> FEATURE:
<223> OTHER INFORMATION: Fully synthetic

<400> SEQUENCE: 9

```
atcatggaga taattaaaat gataaccatc tcgcaaataa ataagtattt tactgttttc     60
gtaacagttt tgtaataaaa aaacctataa atattccgga ttattcatac cgtcccacca    120
tcgggcgc                                                              128
```

```
<210> SEQ ID NO 10
<211> LENGTH: 18
<212> TYPE: DNA
<213> ORGANISM: Artificial Sequence
<220> FEATURE:
<223> OTHER INFORMATION: Fully synthetic

<400> SEQUENCE: 10
actccggaat attaatag                                                    18
```